(12) United States Patent
Oren et al.

(10) Patent No.: US 10,206,712 B2
(45) Date of Patent: Feb. 19, 2019

(54) SURGICAL IMPLEMENT AND METHOD FOR MANIPULATING A BONE

(71) Applicant: T.A.G. Medical Devices—Agriculture Cooperative Ltd., Kibbutz Gaaton (IL)

(72) Inventors: Ran Oren, Kibbutz Gaaton (IL); Aryeh Mirochinik, Akko (IL); Dan Moor, Kibbutz Gaaton (IL); Robert R. Slater, Jr., Folsom, CA (US)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 199 days.

(21) Appl. No.: 13/761,234

(22) Filed: Feb. 7, 2013

(65) Prior Publication Data
US 2013/0204253 A1 Aug. 8, 2013

Related U.S. Application Data

(60) Provisional application No. 61/595,716, filed on May 7, 2012.

(51) Int. Cl.
*A61B 17/56* (2006.01)
*A61B 17/16* (2006.01)
*A61B 17/88* (2006.01)

(52) U.S. Cl.
CPC .............. *A61B 17/56* (2013.01); *A61B 17/16* (2013.01); *A61B 17/8866* (2013.01); *A61B 17/8875* (2013.01)

(58) Field of Classification Search
CPC . A61B 17/8866; A61B 17/8875; A61B 17/16; A61B 17/1613; A61B 17/1615; A61B 17/1617; A61B 17/162; B25B 13/00; B25B 13/44; B25B 23/0007; B25B 23/0028; B25B 23/0035; B25B 23/0042; B25B 23/16; B25B 17/02; B25G 1/002; B25G 1/005; B25G 1/085; B25G 1/102; B25G 1/105; B25G 3/38; B25G 1/043063
See application file for complete search history.

(56) References Cited

U.S. PATENT DOCUMENTS

| | | | |
|---|---|---|---|
| 4,676,703 A * | 6/1987 | Swanson | 408/239 R |
| 7,296,804 B2 | 11/2007 | Lechot et al. | |
| 7,448,301 B1 * | 11/2008 | Cronin | 81/302 |
| 7,988,692 B2 | 8/2011 | Lechot | |
| 8,206,394 B2 | 6/2012 | Stad et al. | |
| 2004/0099102 A1 * | 5/2004 | Vaughan | 81/124.4 |
| 2004/0231468 A1 * | 11/2004 | Odachowski | 81/58.1 |
| 2008/0269768 A1 | 10/2008 | Schwager et al. | |

OTHER PUBLICATIONS

Stryker "Reduction Instruments. Product and Instruction Guide", Stryker Trauma, Brochure, 16 P., 2009.

* cited by examiner

*Primary Examiner* — Kevin T Truong
*Assistant Examiner* — Tracy Kamikawa

(57) ABSTRACT

A surgical bone holding implement for manipulating a bone, comprising a handle and an elongated shaft including a bone engaging tip. The handle is positionable with respect to the elongated shaft between first and second positions, for mounting a drill member on the proximal end of the elongated shaft in one position, and for manipulating the bone by means of the handle in a second position.

19 Claims, 3 Drawing Sheets

SURGICAL IMPLEMENT AND METHOD FOR MANIPULATING A BONE

RELATED APPLICATIONS

This application claims the benefit of priority under 35 USC § 119(e) of U.S. Provisional Patent Application No. 61/595,716 filed Feb. 7, 2012, the contents of which are incorporated herein by reference in their entirety.

FIELD AND BACKGROUND OF THE INVENTION

Several orthopedic surgical procedures require bringing and holding of a bone to the correct location and direction for surgery. As an example, holding of a metacarpal bone of the human hand will be discussed and illustrated.

An implement which has been used for holding a bone of the human hand is shown in FIG. 2. The T-Handle is removable from the shaft after loosening of the screw. The use of the implement involves the following steps: Removing the handle from the shaft; driving the shaft into the bone aided by a drill brace or power drill; re-attaching the handle to the shaft; manipulating and holding the bone by means of the handle. Removal and re-attachment of the handle during the surgical procedure poses some risks which should be preferably avoided.

SUMMARY OF THE INVENTION

The invention provides a bone holding device consisting of a star shaped indexable handle mounted onto an elongated shaft. The distal section of said elongated shaft consists of a pilot drill section with a trocar tip leading to a bone screw thread, and is configured to enable drilling it into the targeted bone. The handle is indexable between a first and a second position. In the first position the proximal section of said elongated shaft, configured to fit a drill chuck, is exposed, enabling the use of a power drill or a drill brace to drive it into the bone. Once the shaft is firmly drilled into the bone, the handle is indexed to the second position, concealing the shaft in a recesses provided in the handle for this purpose. It is now convenient to manipulate and hold the bone by means of the handle.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF MAKING AND USING THE INVENTION

Several embodiments adapting the invention to different bones in the body are possible. All of them can be made using conventional techniques and materials by any person of ordinary skill in the pertinent art. Although the invention is described in a non limiting fashion by an example of its use in a specific location—the metacarpal of the thumb—it should be understood that it can easily be adapted to other similar applications.

Figure 1:
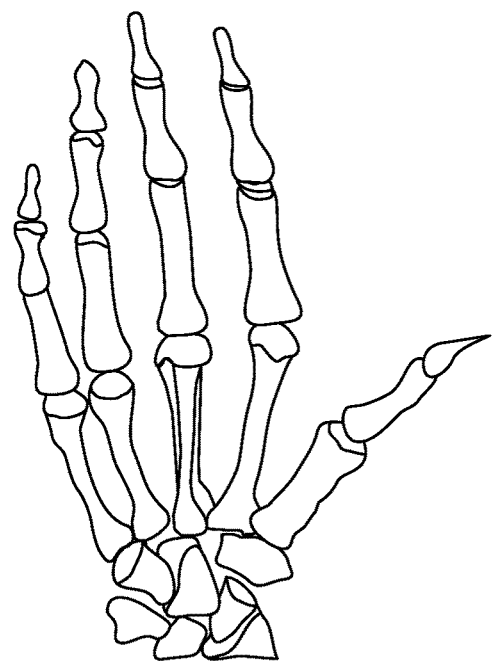
FIG. 1 Shows the bones of the human hand.

FIG. 1 shows the carpal, metacarpal and phalangeal bones of the human hand.

Figure 2:
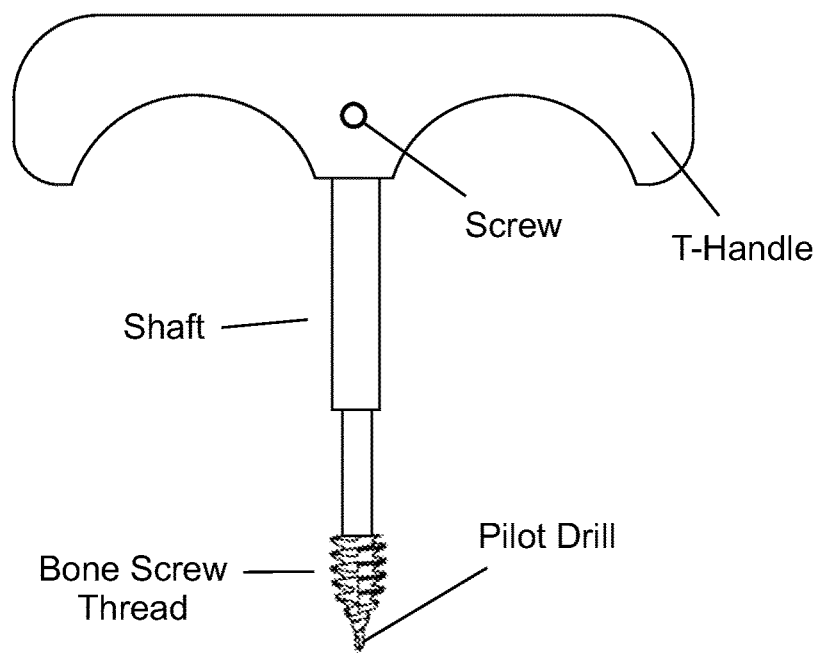
FIG. 2 Bone holder with T-handle (Prior art).

FIG. 2 is an implement currently used for manipulating and holding a bone. The implement has a T-handle, which must be detached and re-attached to the shaft during the surgical procedure.

Figure 3:
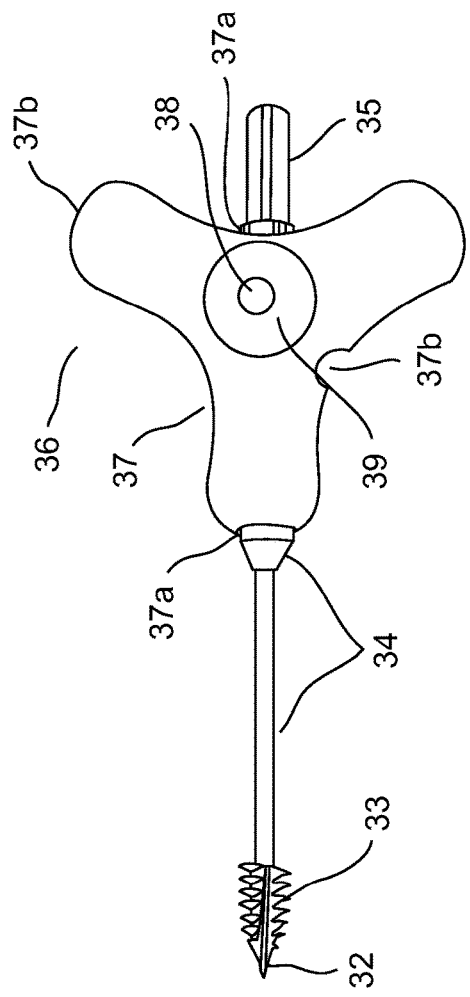
FIG. 3 Is a top view of the preferred embodiment of the invention.

FIG. 3 is a top view of a preferred embodiment of the invention. The elongated shaft generally designated as (31) of the implement, consists of the following sections: pilot drill (32); bone screw thread (33); shank (34) and proximal end, configured to fit a drill chuck (35). The handle assembly, generally designated as (36), consists of the handle body (37); pivot pin (38) and nut (39). The handle assembly is pivotably connected to the elongated shaft and is indexable between a first position wherein a drill chuck can be mounted onto the proximal section of the shaft (as shown in FIG. 3), and a second position wherein the proximal section of the shaft is covered by the handle (as shown in FIG. 6).

Figure 4:
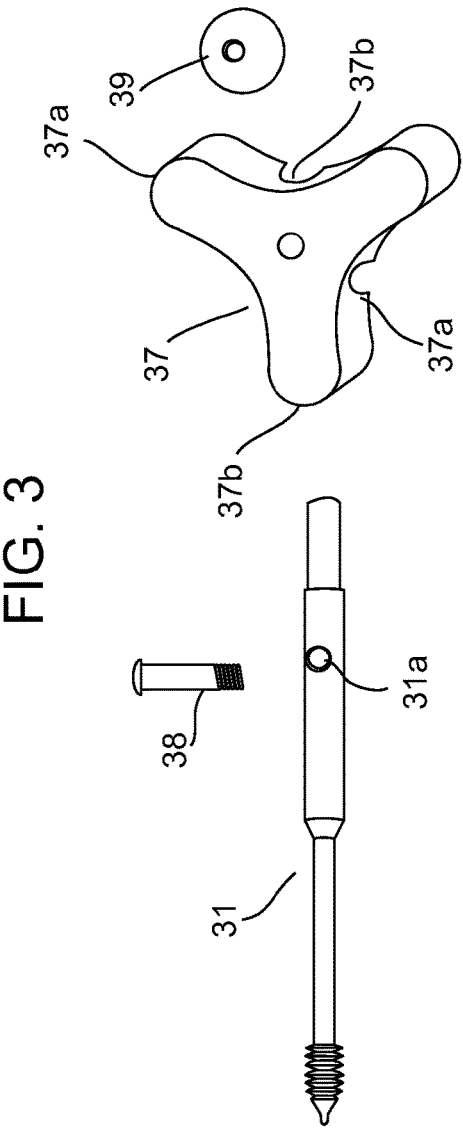
FIG. 4 Shows the parts of the indexable handle of the invention.

FIG. 4 is an exploded view of the implement, showing the elongated shaft (31) and the components of the handle assembly (36). The bore (31a) for mounting the handle is visible. The pivot pin (38) is after assembly rotatable in bore (31a) and is threaded to accept nut (39). Handle body (37) is provided with open slots at (37a and 37b) to accept and cover the elongated shaft. Upon full indexing the shaft snaps into a recess at the bottom of the slots.

Figure 5:
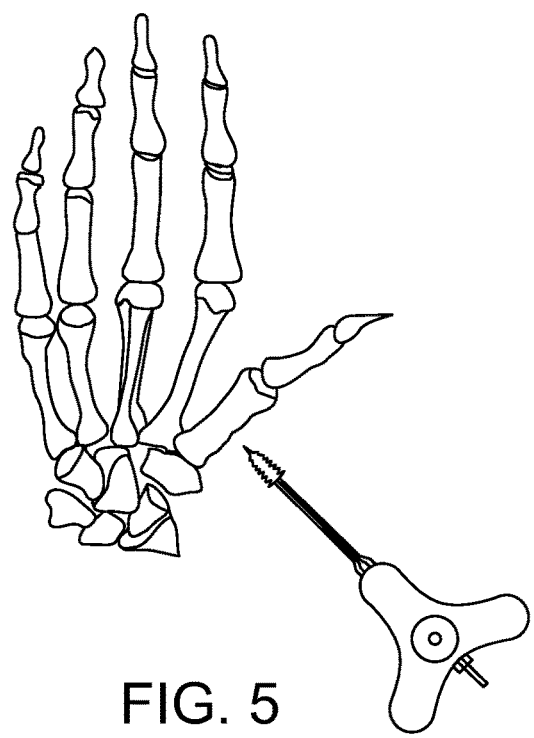
FIG. 5 Shows the handle in its first position, ready to drill the shaft into the metacarpal of the thumb.

FIG. 5 Shows the handle in its first position, ready to drill the shaft into the metacarpal of the thumb.

Figure 6:
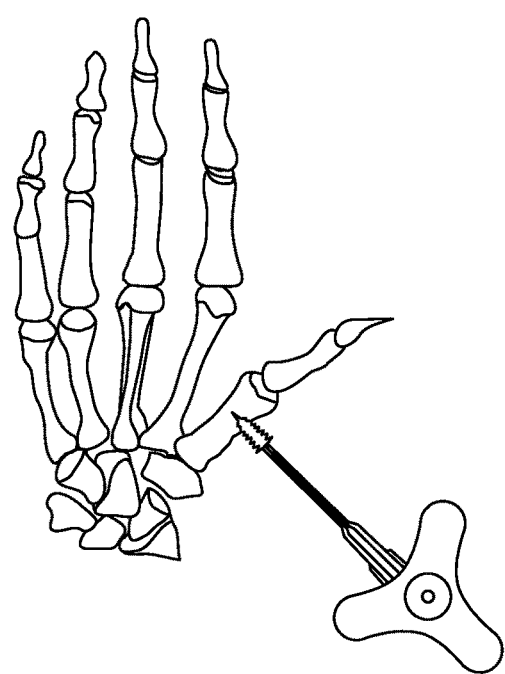
FIG. 6 Shows the implement embedded in the bone, with the handle indexed to its second position.

FIG. 6 Shows the implement embedded in the bone, with the handle indexed to its second position, enabling easy and comfortable holding of the bone.

What is claimed is:

1. A bone holding implement comprising:

an elongated shaft comprising a distal end having a bone engaging tip, a shank, and a proximal end configured to fit a drill chuck; said elongated shaft having a longitudinal axis; and a handle coupled to said elongated shaft, said handle selectively positionable with respect to said elongated shaft, wherein said handle comprises a pivot pin, and a plurality extensions that extend radially outward from said pivot, at least one of said extensions having an underside including an elongate slot extending along a length of said underside, wherein said elongate slot has a longitudinal axis, wherein the handle is pivotably connected to said elongated shaft to be rotated around an axis perpendicular to the shaft between a first position in which a portion of said shaft is received in said elongate slot, with said shaft and said slot being coaxial, with said bone engaging tip protruding out said handle at one location and said proximal end exposed outside said slot for attaching to said drill chuck, and a second position in which said bone engaging tip protrudes out said handle at a second location.

2. The bone holding implement according to claim 1, wherein said bone engaging tip comprises a bone screw thread and a pilot drill.

3. The bone holding implement according to claim 1, wherein said handle is removable from said shaft.

4. The bone holding implement according to claim 1, wherein said handle is star shaped.

5. The bone holding implement according to claim 1, wherein said elongated shaft is configured to snap fit into said handle.

6. The bone holding implement according to claim 1, wherein said shaft comprises a bore for receiving said pivot pin.

7. The bone holding implement according to claim 1, wherein said proximal end of said elongated shaft comprises a polygonal profile.

8. The bone holding implement according to claim 1, wherein said pivot pin comprises a thread.

9. The bone holding implement according to claim 1, wherein said bone engaging tip is shaped and sized to engage a metacarpal bone of the human hand.

10. The bone holding implement according to claim 1, wherein said handle is coupled to one side of said elongated shaft, in both said first and second positions.

11. The bone holding implement according to claim 1, wherein an underside of said handle is coupled to said elongated shaft.

12. The bone holding implement according to claim 1, wherein said plurality of extensions include at least three extensions.

13. The bone holding implement according to claim 1, wherein in said first position, said proximal end of said shaft protrudes out said handle at said second location.

14. The bone holding implant according to claim 1, wherein said handle includes a top side opposite said underside wherein in said second position, said proximal end of said shaft is covered by said handle when looking at said top side.

15. The bone holding implant according to claim 1, wherein said handle is rotatably attached to said shaft by said pivot pin.

16. The bone holding implement of claim 1, wherein said handle remains attached to said shaft while being rotated between said first and said second positions.

17. The bone holding implement according to claim 1, wherein in said second position, said proximal end of said shaft is received in the elongate slot.

18. The bone holding implement according to claim 1, wherein in said first position, said shank is received in the elongate slot.

19. The bone holding implement according to claim 18, wherein in said second position, said shank is received in a second elongate slot.

* * * * *

UNITED STATES PATENT AND TRADEMARK OFFICE
CERTIFICATE OF CORRECTION

PATENT NO. : 10,206,712 B2
APPLICATION NO. : 13/761234
DATED : February 19, 2019
INVENTOR(S) : Ran Oren et al.

Page 1 of 1

It is certified that error appears in the above-identified patent and that said Letters Patent is hereby corrected as shown below:

On the Title Page

In item (60) Related U.S. Application Data:
"May 7, 2012" should be changed to --February 7, 2012--

Signed and Sealed this
Eighteenth Day of June, 2019

Andrei Iancu
*Director of the United States Patent and Trademark Office*